US011464557B2

United States Patent
Tosi et al.

(10) Patent No.: US 11,464,557 B2
(45) Date of Patent: Oct. 11, 2022

(54) METHOD OF DISTRIBUTED TEMPERATURE SENSING DURING THERMAL TUMOR ABLATION USING A FIBER OPTIC TEMPERATURE SENSOR WITH A LINEARLY CHIRPED BRAGG GRATING

(71) Applicant: "NAZARBAYEV UNIVERSITY RESEARCH AND INNOVATION SYSTEM", Astana (KZ)

(72) Inventors: Daniele Tosi, Astana (KZ); Nurlan Sabitovich Zhakin, Almaty (KZ); Sanzhar Botabekovich Korganbayev, Almaty (KZ)

(73) Assignee: PRIVATE INSTITUTION "NAZARBAYEV UNIVERSITY RESEARCH AND INNOVATION SYSTEM", Astana (KZ)

( * ) Notice: Subject to any disclaimer, the term of this patent is extended or adjusted under 35 U.S.C. 154(b) by 1046 days.

(21) Appl. No.: 16/090,354

(22) PCT Filed: Apr. 4, 2017

(86) PCT No.: PCT/KZ2017/000006
§ 371 (c)(1),
(2) Date: Oct. 1, 2018

(87) PCT Pub. No.: WO2017/176101
PCT Pub. Date: Oct. 12, 2017

(65) Prior Publication Data
US 2019/0113395 A1    Apr. 18, 2019

(30) Foreign Application Priority Data
Apr. 5, 2016  (KZ) ................. 2016/0317.1

(51) Int. Cl.
*A61B 18/04*    (2006.01)
*G01K 13/20*    (2021.01)
(Continued)

(52) U.S. Cl.
CPC .......... *A61B 18/04* (2013.01); *G01K 11/3206* (2013.01); *G01K 13/20* (2021.01);
(Continued)

(58) Field of Classification Search
CPC .......... A61B 18/04; A61B 2018/00577; A61B 2018/00714; A61B 2018/00791; G01K 13/20; G01K 13/00; G01K 11/3206
See application file for complete search history.

(56) References Cited

U.S. PATENT DOCUMENTS

| 9,151,811 | B2 * | 10/2015 | Jester | G01K 11/3206 |
| 2002/0077627 | A1 * | 6/2002 | Johnson | A61B 18/1477 606/41 |

(Continued)

FOREIGN PATENT DOCUMENTS

| FR | 2 772 488 A1 | 6/1999 |
| KZ | 32496 B | 11/2017 |

(Continued)

OTHER PUBLICATIONS

International Search Report and Written Opinion dated Sep. 7, 2017 in counterpart application No. PCT/KZ2017/000006 (w/ English translation; 9 pages).
(Continued)

*Primary Examiner* — Linda C Dvorak
*Assistant Examiner* — Annabeth E Rodriguez
(74) *Attorney, Agent, or Firm* — Seckel IP, PLLC

(57) ABSTRACT

An effective and highly accurate method for measuring temperature during thermal tumor ablation to increase ablation accuracy includes installing a fiber optic temperature
(Continued)

sensor with a linearly chirped (the variation of the refractive index has a period growing in an algebraic progression) Bragg grating with a length of 1.4-6 cm and a diameter of 80-300 μm using a catheter directly on the tumor. Through the fiber optic sensor with a length of 1.4-6 cm and a diameter of 80-300 μm is passed a light spectrum, which undergoes backscatter due to the Bragg grating, dependent on the temperature acting on the sensor. Subsequently, using the backscatter light spectrum decoding software, developed according to the fiber optic cable parameters, the temperature profile is displayed on the computer. The method has applications in medicine, in particular oncology.

19 Claims, 1 Drawing Sheet

(51) Int. Cl.
  *G01K 11/3206* (2021.01)
  *A61B 18/00* (2006.01)
  *G01K 13/00* (2021.01)
(52) U.S. Cl.
  CPC .............. *A61B 2018/00577* (2013.01); *A61B 2018/00714* (2013.01); *A61B 2018/00791* (2013.01); *G01K 13/00* (2013.01)

(56) References Cited

U.S. PATENT DOCUMENTS

| | | | | |
|---|---|---|---|---|
| 2003/0133656 A1* | 7/2003 | Baldwin | ............ | G02B 6/02204 385/37 |
| 2003/0236626 A1* | 12/2003 | Schroeder | ............... | G01K 15/00 374/E11.015 |
| 2008/0275440 A1* | 11/2008 | Kratoska | ............ | A61B 18/1477 606/41 |
| 2014/0188103 A1* | 7/2014 | Millett | ............... | A61B 18/1492 607/113 |
| 2014/0206988 A1* | 7/2014 | Ramachandran | .. | G01K 11/3206 600/478 |
| 2017/0074688 A1* | 3/2017 | Crickmore | ......... | G01K 11/3206 |

FOREIGN PATENT DOCUMENTS

| | | |
|---|---|---|
| RU | 75292 U1 | 8/2008 |
| WO | 2015/117128 A1 | 8/2015 |

OTHER PUBLICATIONS

Webb et al., "First in-vivo trials of a fiber Bragg grating based temperature profiling system", J. of Biomedical Optics, vol. 5, No. 1, pp. 45-50, Jan. 2000 (in English).

Xu et al., "Temperature-independent strain sensor using a chirped Bragg grating in a tapered optical fibre", Electronics Letters, vol. 31, No. 10, pp. 823-825, May 11, 1995 (in English).

Gnyawali et al., "Temperature measurement on tissue surface during laser irradiation", Med. Bio. Eng. Comput., vol. 46, pp. 159-168, 2008 (in English).

Manns et al., "In Situ Temperature Measurements With Thermocouple Probes During Laser Interstitial Thermotherapy (LITT)", Lasers in Surgery and Medicine, vol. 23, pp. 94-103, 1998 (in English).

Kazhakstan Office Action dated Jun. 8, 2017 in priority application No. KZ2016/0317.1 (w/ partial English translation; 5 pages).

Kazhakstan Notification of Grant dated Sep. 25, 2017 in priority application No. KZ2016/0317.1 (w/ partial English translation; 4 pages).

Patel et al., "Methods for Providing Probe Position and Temperature Information on MR Images During Interventional Procedures", IEEE Transactions on Medical Imaging, vol. 17, No. 5, pp. 794-802, Oct. 1998 (in English; cited in Office Action dated Jun. 8, 2017 in priority KZ application).

Yegorenkov, "Treatment of Malignant Liver Tumors Using the Methods of Local Destruction", Practical Oncology, vol. 9, No. 4, pp. 202-208, 2008 (w/English partial translation; cited in Office Action dated Jun. 8, 2017 in priority KZ application; 8 pages).

"The Exablate Techology for Tumor Removal", Oct. 5, 2010, http://is-med.com/publ/2-a1-0-409 (w/English partial translation; cited in Office Action dated Jun. 8, 2017 in priority KZ application; 24 pages).

Ulashchik, "The role of local hyperthermia in oncology: applications of a magnetic field, laser radiation, and ultrasound", Questions of health resort study, physiotherapy and physical therapy, vol. 2, pp. 48-57 (w/English partial translation; cited in Office Action dated Jun. 8, 2017 in priority KZ application; 16 pages).

* cited by examiner

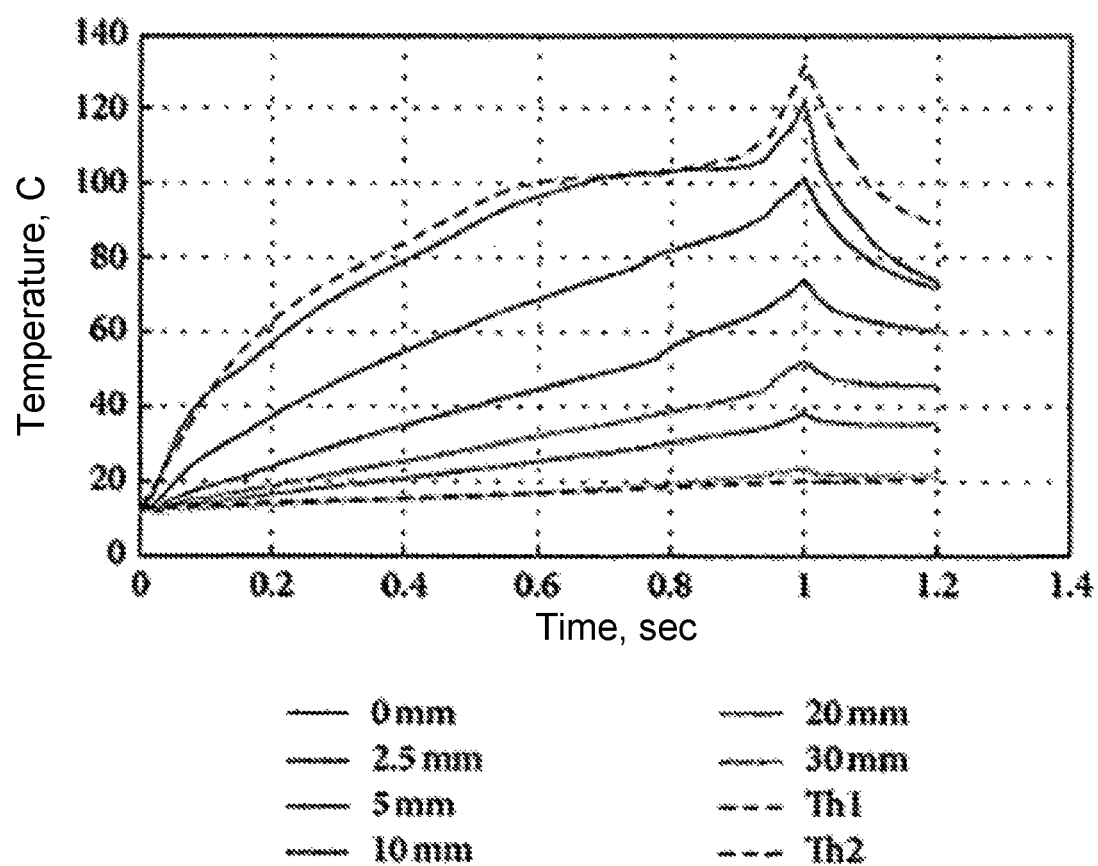

METHOD OF DISTRIBUTED TEMPERATURE SENSING DURING THERMAL TUMOR ABLATION USING A FIBER OPTIC TEMPERATURE SENSOR WITH A LINEARLY CHIRPED BRAGG GRATING

The invention relates to medicine, in particular to oncology, and is intended to measure temperature during thermal tumor ablation.

BACKGROUND ART

There is a known method of measuring temperature using an infrared camera, proposed by Gnyawali and coauthors (Gnyawali S C, Chen Y, Wu F, Bartels K E, Wicksted J P, Liu H, Sen C K and Chen W R 2008 Temperature measurement on tissue surface during laser irradiation Med. Biol. Eng. Comput. 46 159-68).

The disadvantages of the method lie in the impossibility of invasive measurement and in the need for an absence of tissues between the camera and the organ which has a tumor.

Also known is a method using thermocouples and thermistors (Manns F, Milne P J, Gonzalez-Cirre X, Denham D B, Parel J M and Robinson D S 1998 In situ temperature measurement with thermocouple probes during laser interstitial thermotherapy (LITT): quantification and correction of a measurement artifact Laser Surg. Med. 23 94-103).

These sensors are subject to thermal and electromagnetic effects, and distributed temperature sensing is also impossible.

The closest analogue is the use of a series of fiber optic temperature sensors with a uniform Bragg grating, which has a periodic variation of the refractive index with a constant period. This method was first proposed in the journal Biomedical Optics (Webb D J, Hathaway M W, Jackson D A, Jones S, Zhang L and Bennion I 2000 First in-vivo trials of a fiber Bragg grating based temperature profiling system *J. Biomed. Opt.* 5 45-50).

A set of consecutive sensors creates quasi-distributed temperature sensing (sensing a set of points).

The disadvantages of the prototype lie in the low resolution, which has a negative effect on the accuracy of thermal ablation.

SUMMARY OF THE INVENTION

The object of the invention is to develop an effective and highly accurate method for measuring temperature during thermal tumor ablation.

The technical result of the invention is to increase the quality of patient treatment by increasing the accuracy of thermal tumor ablation.

The technical result is achieved in that the claimed method includes the installation of a fiber optic temperature sensor with a linearly chirped (the variation of the refractive index has a period growing in an algebraic progression) Bragg grating with a length of 1.4-6 cm and a diameter of 80-300 μm using a catheter directly on the tumor.

Through the fiber optic sensor with a length of 1.4-6 cm and a diameter of 80-300 μm is passed a light spectrum, which undergoes backscatter due to the Bragg grating, dependent on the temperature acting on the sensor. Subsequently, using a backscatter spectrum decoding software, developed according to the fiber optic cable parameters, a temperature profile is obtained, which is used for more accurate tumor ablation and prediction of heat distribution in the organ.

The decoding is done through a computer, connected to equipment consisting of a source of light and a detector.

New in the claimed solution is the use of a linearly chirped Bragg grating in the fiber optic cable and a backscatter light spectrum decoding software to obtain a temperature profile. This ensures distributed temperature sensing, short sensing time and high resolution (50-100 μm) and as a result allows for the performance of a more accurate, high-quality thermal tumor ablation.

BRIEF DESCRIPTION OF THE DRAWINGS

FIG. 1 shows the temperatures of 6 fiber optic cables at different distances and the temperatures measured by two thermistors (B57861 Epcos, Munich, Germany; accuracy ±0.2° C.), one of which is placed on the ablation equipment, and the second one at a distance of 3 cm.

DETAILED DESCRIPTION OF PARTICULAR EMBODIMENTS

The method of temperature sensing is embodied as follows.

First a fiber optic cable with a length of sensor 1.4-6 cm and a diameter of 80-300 μm is placed on the tumor, depending on its size, using a catheter. The cable is connected to a broadband light source, and a detector. A coupler, connected to the light source, the light source and the light detector are connected to a computer. Using the backscatter light spectrum decoding software, developed according to the fiber optic cable parameters, the temperature profile is displayed on the computer.

EMBODIMENTS OF THE METHOD

Example 1

Patient F., age 54 came with a diagnosis of lung cancer. What was detected was a malignant tumor of medium size on the right lung. The tumor was diagnosed and localized. It required removal by thermal ablation. After preparation of the patient, a surgical incision was performed and a fiber optic sensor with a length of 1.4 cm and a diameter of 80 μm was placed on the tumor; the cable was then connected to the equipment and computer. Using the software, the current temperature of the tumor was displayed on the monitor. With the change of profile and increase in the temperature of healthy tissues, the physician stopped the ablation process and repositioned the ablation instrument for accurate removal of the tumor. As a result, there was complete removal of the tumor.

Example 2

Patient N., age 42 came with a diagnosis of liver cancer. What was detected was a large malignant tumor. The tumor was diagnosed and localized. It required removal by thermal ablation. The boundaries of the tumor on the organ were determined. After preparation of the patient, a surgical incision was performed and a fiber optic sensor with a length of 4.2 cm and a diameter of 250 μm was placed on the tumor; the cable was then connected to the equipment and computer. Using the software, the current temperature of the tumor was displayed on the monitor. No ablation temperature was observed outside the boundaries of the tumor. No repositioning of the ablation instrument was required. The process continued until complete removal of the tumor.

Example 3

Patient V., age 41 came with a diagnosis of lung cancer. What was detected was a large malignant tumor on the left lung. The tumor was diagnosed and localized. It required removal by thermal ablation. After preparation of the patient, a surgical incision was performed and a fiber optic sensor with a length of 6 cm and a diameter of 300 μm was placed on the tumor; the cable was then connected to the equipment and computer. Using the software, the current temperature of the tumor was displayed on the monitor. With the change of profile and increase in the temperature of healthy tissues, the physician stopped the ablation process and repositioned the ablation instrument for accurate removal of the tumor. As a result, there was complete removal of the tumor.

FIG. 1 shows the temperatures of 6 fiber optic cables at different distances and the temperatures measured by two thermistors (B57861 Epcos, Munich, Germany; accuracy ±0.2° C.), one of which is placed on the ablation equipment, and the second one at a distance of 3 cm. As can be seen, the difference between the results of the fiber optic cables and the thermistors is minor. The reasons for the difference are the position of the thermistor within the ablation instrument and the thermal effect on the thermistor during ablation.

As can be seen from the table, the spatial resolution of the linear chirped fiber optic sensor is significantly better than the closest analogue. Therefore, the quality of thermal ablation increases. Accuracy for the proposed invention is lower than the closest analogue; nonetheless, a 0.2° C. error does not affect the ablation process.

The method is invasive, the sensor is placed on the tumor, therefore, the accuracy of measurements is increased, which decreases the likelihood of ablation of healthy tissues.

TABLE 1

Comparison of the Invention to the Closest Analogue

| Technology | Resolution | Accuracy |
| --- | --- | --- |
| Prototype | 1-20 mm | 0.1° C. |
| Claimed Method | 50-100 μm | 0.2° C. |

The invention claimed is:

1. An invasive method for surgical thermal treatment of a human patient with a cancer, wherein the invasive method comprising:
    detecting a malignant tumor on an organ,
    localizing boundaries of the malignant tumor,
    performing of a surgical incision,
    placing of a fiber optic temperature sensor directly on the malignant tumor with the help of a catheter through the surgical incision, the fiber optic temperature sensor comprising a Bragg grating cable, and
    removing of the malignant tumor by thermal ablation using a thermal ablating instrument together with monitoring of a current distributed temperature profile of the malignant tumor along the optic temperature sensor, the current distributed temperature profile being continuously measured by the optic temperature sensor during the thermal ablation,
    wherein the Bragg grating cable includes a linearly chirped Bragg grating,
    wherein a length of the fiber optic temperature sensor is in a range of from 1.4 cm to 6 cm, and
    wherein a diameter of the fiber optic temperature sensor is in a range of from 80 μm to 300 μm,
    wherein the Bragg grating cable is connected to a coupler during the thermal ablation,
    wherein the coupler is connected to a light source adapted to generate an outgoing light spectrum passed through the fiber optic temperature sensor,
    wherein the coupler is also connected to a light detector adapted to detect a backscatter of a reflected light from the fiber optic temperature sensor, the reflected light backscatter being due to the linearly chirped Bragg grating dependent on temperature acting on the fiber optic temperature sensor, and
    wherein the coupler is also connected to a computer adapted to decode a spectrum of the reflected light backscatter in the current distributed temperature profile of the malignant tumor along the optic temperature sensor.

2. The invasive method for surgical thermal treatment according to claim 1, wherein the method comprises:
    stopping the thermal ablation process if the current distributed temperature profile of the malignant tumor changes, and
    repositioning the thermal ablating instrument before a resumption of the thermal ablation process.

3. The invasive method for surgical thermal treatment according to claim 1, wherein the method comprises connecting the Bragg grating cable to the coupler.

4. The invasive method for surgical thermal treatment according to claim 1, wherein the computer comprises a monitor, and wherein the invasive method for surgical thermal treatment comprises displaying the current distributed temperature profile of the malignant tumor on the monitor during the thermal ablation.

5. The invasive method for surgical thermal treatment according to claim 1, wherein a spatial resolution of the fiber optic temperature sensor is in a range of from 50 μm to 100 μm.

6. The invasive method for surgical thermal treatment according to claim 1, wherein a temperature accuracy of the fiber optic temperature sensor is 0.2° C.

7. The invasive method for surgical thermal treatment according to claim 1, wherein the malignant tumor is detected on a lung.

8. The invasive method for surgical thermal treatment according to claim 7, wherein the length of the fiber optic temperature sensor is 1.4 cm and wherein the diameter of the fiber optic temperature sensor is 80 μm.

9. The invasive method for surgical thermal treatment according to claim 7, wherein the length of the fiber optic temperature sensor is 6 cm and wherein the diameter of the fiber optic temperature sensor is 300 μm.

10. The invasive method for surgical thermal treatment according to claim 1, wherein the malignant tumor is detected on a liver.

11. The invasive method for surgical thermal treatment according to claim 10, wherein the length of the fiber optic temperature sensor is 4.2 cm and wherein the diameter of the fiber optic temperature sensor is 250 μm.

12. An invasive method of distributed temperature sensing during thermal tumor ablation using a fiber optic temperature sensor comprising using a Bragg grating cable during the thermal ablation,
    wherein the method comprises placing the fiber optic temperature sensor directly on a tumor, wherein the Bragg grating cable includes a linearly chirped Bragg grating, wherein a length of the fiber optic temperature sensor is in a range of from 1.4 cm to 6 cm, and wherein a diameter of the fiber optic temperature sensor is in a range of from 80 μm to 300 μm, wherein the Bragg grating cable is connected to a coupler during the thermal ablation, wherein the coupler is connected to a light source adapted to generate an outgoing light spectrum passed through the fiber optic temperature sensor, wherein the coupler is also connected to a light detector adapted to detect a backscatter of a reflected light from the fiber optic temperature sensor, the reflected light backscatter being due to the linearly chirped Bragg grating dependent on temperature acting on the fiber optic temperature sensor, and wherein the coupler is also connected to a computer adapted to decode a spectrum of the reflected light backscatter in the current distributed temperature profile of the malignant tumor along the optic temperature sensor.

13. The invasive method of distributed temperature sensing according to claim 12, wherein the method comprises connecting the Bragg grating cable to the coupler.

14. The invasive method of distributed temperature sensing according to claim 12, wherein the computer comprises a monitor, and wherein the invasive method of distributed temperature sensing comprises displaying the current distributed temperature profile of the malignant tumor on the monitor during the thermal ablation.

15. The invasive method of distributed temperature sensing according to claim 12, wherein a spatial resolution of the fiber optic temperature sensor is in a range of from 50 μm to 100 μm.

16. The invasive method of distributed temperature sensing according to claim 12, wherein a temperature accuracy of the fiber optic temperature sensor is 0.2° C.

17. The invasive method of distributed temperature sensing according to claim 12, wherein the distributed temperature sensing is performed during ablation of the tumor from a lung.

18. The invasive method of distributed temperature sensing according to claim 12, wherein the distributed temperature sensing is performed during ablation of the tumor from a liver.

19. The invasive method of distributed temperature sensing according to claim 18, wherein the length of the fiber optic temperature sensor is 4.2 cm and wherein the diameter of the fiber optic temperature sensor is 250 μm.

* * * * *